(12) United States Patent
Cheng et al.

(10) Patent No.: US 9,705,239 B2
(45) Date of Patent: Jul. 11, 2017

(54) FLEXIBLE ELECTRODE ASSEMBLY AND APPARATUS FOR MEASURING ELECTROPHYSIOLOGICAL SIGNALS

(75) Inventors: Arthur Cheng, Bellevue Hill (AU); Alexander Klistorner, Mt Colah (AU); Stuart Lindsay Graham, Pymble (AU)

(73) Assignee: OBJECTIVISION LIMITED, Eveleigh, NSW (AU)

( * ) Notice: Subject to any disclaimer, the term of this patent is extended or adjusted under 35 U.S.C. 154(b) by 1048 days.

(21) Appl. No.: 12/439,211

(22) PCT Filed: Aug. 30, 2007

(86) PCT No.: PCT/AU2007/001254
§ 371 (c)(1),
(2), (4) Date: Sep. 1, 2009

(87) PCT Pub. No.: WO2008/025078
PCT Pub. Date: Mar. 6, 2008

(65) Prior Publication Data
US 2010/0016701 A1   Jan. 21, 2010

(30) Foreign Application Priority Data
Aug. 31, 2006   (AU) ................ 2006904755

(51) Int. Cl.
*A61B 5/04* (2006.01)
*H01R 13/52* (2006.01)
*A61B 5/0408* (2006.01)

(52) U.S. Cl.
CPC ..... *H01R 13/5224* (2013.01); *A61B 5/04085* (2013.01)

(58) Field of Classification Search
CPC .............. A61B 5/04085; A61B 5/6833; A61B 5/040087; A61B 5/0006; A61B 5/053; A61B 5/6832; A61B 5/0402; A61B 5/6804; A61B 5/6805; A61B 5/381; A61B 5/486; A61B 5/6824; A61B 2560/0412; A61N 1/0492; A61N 1/00; A61N 1/08
(Continued)

(56) References Cited

U.S. PATENT DOCUMENTS 4,967,038 A    10/1990  Gevins et al.
5,224,479 A *   7/1993  Sekine .................... 600/389
(Continued)

FOREIGN PATENT DOCUMENTS

WO          97/14346 A2      4/1997

OTHER PUBLICATIONS

International Search Report for PCT/AU2007/001254.

*Primary Examiner* — Joseph Stoklosa
*Assistant Examiner* — Brian M Antiskay
(74) *Attorney, Agent, or Firm* — Brooks Kushman P.C.

(57) ABSTRACT

A flexible electrode assembly comprises a central portion having electrical contacts disposed thereon and a plurality of elongated portions extending radially outwards from the central portion. One or more of the elongated portions has an electrode disposed in the vicinity of a distal end thereof. The electrodes are electrically coupled to respective ones of the electrical contacts disposed on the central portion. An apparatus for measuring electrophysiological signals in a human or animal body that incorporates the flexible electrode assembly is also disclosed.

15 Claims, 5 Drawing Sheets

(58) Field of Classification Search
USPC ......... 600/382, 384, 386, 390–393, 508–510
See application file for complete search history.

(56) References Cited

U.S. PATENT DOCUMENTS

| | | | | |
|---|---|---|---|---|
| 5,738,104 | A * | 4/1998 | Lo et al. ........................ | 600/521 |
| 6,024,702 | A | 2/2000 | Iversen | |
| 6,047,202 | A * | 4/2000 | Finneran et al. .............. | 600/382 |
| 6,456,872 | B1 * | 9/2002 | Faisandier ......... | A61B 5/04085 600/390 |
| 6,605,046 | B1 * | 8/2003 | Del Mar ............ | A61B 5/04085 128/917 |
| 6,847,836 | B1 | 1/2005 | Sujdak | |
| 7,206,630 | B1 * | 4/2007 | Tarler ........................... | 600/509 |
| 7,460,899 | B2 * | 12/2008 | Almen ........................ | 600/509 |
| 2005/0004490 | A1 * | 1/2005 | Organ et al. .................. | 600/547 |
| 2008/0139953 | A1 * | 6/2008 | Baker et al. .................. | 600/509 |

\* cited by examiner

FLEXIBLE ELECTRODE ASSEMBLY AND APPARATUS FOR MEASURING ELECTROPHYSIOLOGICAL SIGNALS

FIELD OF THE INVENTION

The present invention relates to an apparatus for measuring electrophysiological signals from human or animal bodies and to a flexible assembly of electrodes for use with such an apparatus.

BACKGROUND

The measurement of electrophysiological signals from a human or animal body generally requires electrodes to be maintained substantially in contact with the subject body. As such signals are generally of small magnitude (e.g., micro volts or less), the electrodes are typically made from, or coated with, gold or another highly conductive material. Conventional electrodes are generally electrically coupled to an amplifier or other signal processing apparatus by means of high conductivity wires that are required to be electrically connected to the actual electrodes. However, the presence of wires connected directly to electrodes in an electrode assembly is inconvenient, particularly, for example, when the electrode assembly is to be applied to a human head. Furthermore, some means of strain relief is necessary to prevent the wires becoming detached from the electrodes as the electrode assembly is moved or manipulated.

A disadvantage associated with soldering the wires to the electrodes is that potentials are generated when the wires and electrodes are of dissimilar conductive metals (due to the galvanic effect). As the electrophysiological signals themselves are of small magnitude, such parasitic potentials constitute substantial unwanted interference. Crimping of the wires to the electrodes is thus advantageous compared to soldering, but disadvantageously requires the electrodes to incorporate a crimping portion. This translates into specialized electrodes of relatively higher cost, which consequently may not be disposable.

A need exists for improved apparatuses for measuring electrophysiological signals from human or animal bodies.

SUMMARY

Aspects of the present invention provide a flexible electrode assembly and an apparatus for measuring electrophysiological signals in a human or animal body.

One aspect of the present invention provides a flexible electrode assembly comprising a central portion having electrical contacts disposed thereon and a plurality of elongated portions extending radially outwards from the central portion. One or more of the elongated portions has an electrode disposed in the vicinity of a distal end thereof. The electrodes are electrically coupled to respective ones of the electrical contacts disposed on the central portion.

The flexible electrode assembly may be of a unitary structure. Furthermore, the flexible electrode assembly may comprise a flexible printed circuit board 101 and the electrical contacts and the electrodes may comprise conductive portions of the flexible printed circuit board 101.

In one embodiment, the flexible electrode assembly comprises four elongated portions disposed at substantially 90 degree intervals around the central portion.

Another aspect of the present invention provides an apparatus for measuring electrophysiological signals in a human or animal body. The apparatus comprises a support structure comprising a central portion and a plurality of elongated portions extending radially outwards from the central portion and a flexible electrode assembly comprising a plurality of elongated portions each having an electrode disposed thereon. The flexible electrode assembly is mounted on the support structure such that the elongated portions of the flexible electrode assembly each extend along a respective elongated portion of the support structure.

The plurality of elongated portions of the support structure may be resiliently deformable and/or the flexible electrode assembly may be of unitary structure.

The apparatus may further comprise an amplifier module for amplifying electrophysiological signals detected by the electrodes. The electrodes may be electrically connected to the amplifier by way of compressed contact of electrically conducting surfaces.

The apparatus may further comprise attachment means for attaching the apparatus to a human or animal body. The attachment means may comprise a strap which, when under tension, causes the elongated portions of the support structure to deform such that contact between the electrodes and the human or animal body is substantially maintained.

The flexible electrode assembly and/or apparatus may be disposable.

Another aspect of the present invention provides an apparatus for measuring electrophysiological signals in a human or animal body. The apparatus comprises a plurality of electrodes for detecting electrophysiological signals, a support structure for applying the electrodes to a human or animal body such that an electrically conductive path is maintained between the electrodes and the human or animal body, and an electronic circuit for processing the electrophysiological signals detected by the electrodes. The electrodes and the electronic circuit are electrically connected by a solderless connection.

BRIEF DESCRIPTION OF THE DRAWINGS

Embodiments are described hereinafter, by way of example only, with reference to the accompanying drawings in which.

DETAILED DESCRIPTION

Figure 1:
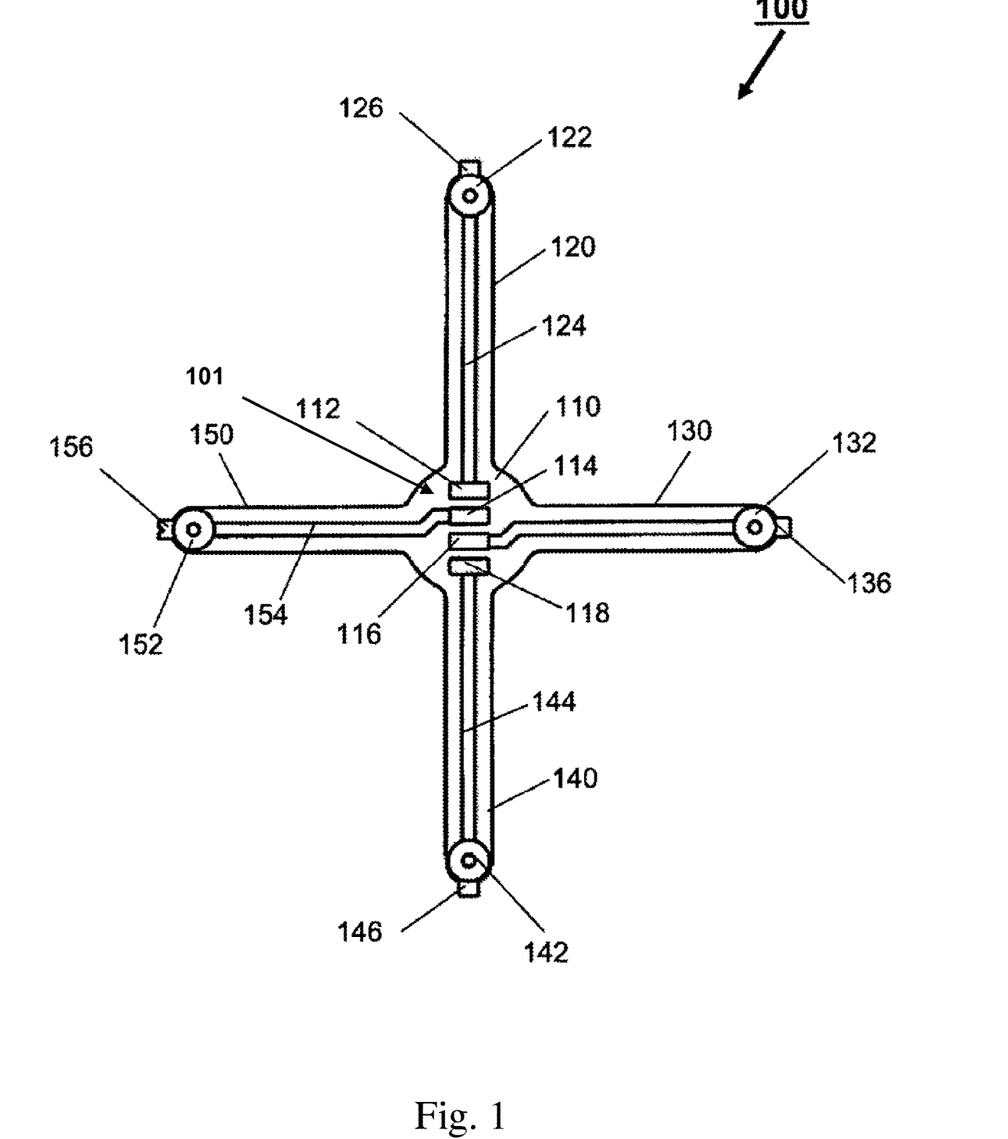
FIG. 1 is a plan view of a flexible electrode assembly in accordance with an embodiment of the present invention.

FIG. 1 shows a flexible electrode assembly 100 in accordance with an embodiment of the present invention. The flexible electrode assembly 100 comprises a central portion 110 having electrical contacts 112, 114, 116 and 118 disposed thereon, and a plurality of elongated portions 120, 130, 140 and 150, each extending radially outwards from the central portion 110. The elongated portions 120, 130, 140 and 150 each have an electrode 122, 132, 142 and 152 disposed in the vicinity of a distal end of a respective elongated portion 120, 130, 140 and 150. Each of the electrodes 122, 132, 142 and 152 are electrically connected to a respective electrical contact 112, 114, 116 and 118 via a respective electrically conductive path 124, 134, 144 and 154.

The flexible electrode assembly 100 may comprise a flexible printed circuit board 101 in which the electrical contacts 112, 114, 116 and 118 and the electrodes 122, 132, 142 and 152 comprise electrically conductive pads and the electrically conductive paths 124, 134, 144 and 154 comprise electrically conductive tracks. The flexible printed circuit board 101 typically comprises a double-sided printed circuit board and the electrodes 122, 132, 142 and 152 typically comprise electrically conductive pads on the underside of the double-sided flexible printed circuit board 101 that correspond to the electrically conductive pads on the upperside of the flexible printed circuit board 101, shown as electrodes 122, 132, 142 and 152 in FIG. 1. The corresponding upper- and lower-side conductive pads are connected electrically by way of plated through-holes, a technique well known and widely practiced in the in the printed circuit board manufacturing arts.

The flexible electrode assembly 100 of FIG. 1 is shown with four (4) elongated portions disposed at substantially 90 degree intervals around the central portion. However, the skilled reader will appreciate that a different numbers and/or configurations of elongated portions may be practiced. Different numbers of electrodes may also be practiced. For example, a particular elongated portion may have no electrodes disposed thereon or more than one electrode disposed thereon.

As may be seen from FIG. 1, the electrodes 122, 132, 142 and 152 have holes in the centre thereof. Although not essential, these holes assist application of a conductive gel between the electrode and a body the electrode is in contact with. The conductive gel improves detection of electrophysiological signals from the body by the electrodes.

Figure 2A:
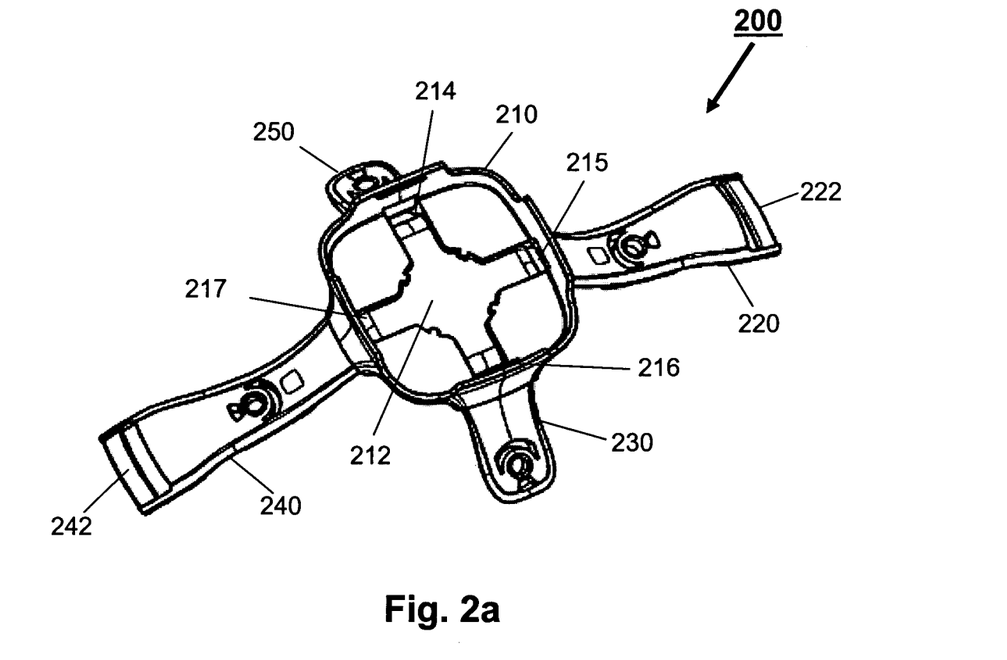
FIGS. 2a and 2b are a perspective view and a front view, respectively, of a support structure for accommodating a flexible electrode assembly in accordance with an embodiment of the present invention.
Figure 2B:
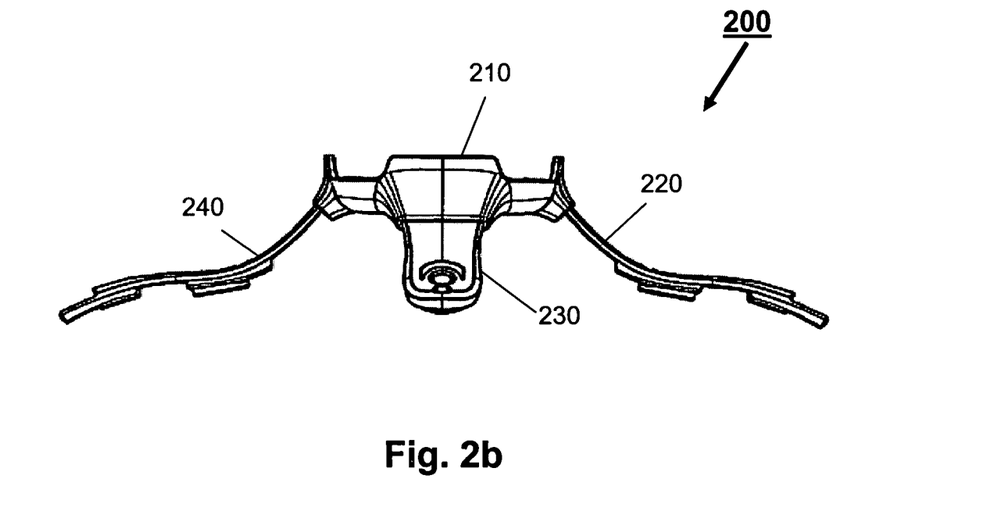

FIGS. 2a and 2b show perspective and front views, respectively, of a support structure 200 for accommodating a flexible electrode assembly in accordance with an embodiment of the present invention. The support structure 200 may be used to accommodate the flexible electrode assembly 100 described hereinbefore with reference to FIG. 1.

Referring to FIG. 2, the support structure 200 comprises a central portion 210 and elongated portions 220, 230, 240 and 250 extending radially outwards from the central portion 210. The central portion 210 may comprise a recessed portion 212 for accommodating the flexible electrode assembly 100 described hereinbefore with reference to FIG. 1. The central portion 210 further comprises substantially rectangular slots 214, 215, 216 and 217 for the elongated portions 120, 130, 140 and 150 of the flexible electrode assembly 100 to pass through such that the elongated portions 120, 130, 140 and 150 are disposed on the underside of the elongated portions 220, 230, 240 and 250 and such that the portions or surfaces of the electrodes 122, 132, 142 and 152 that are to be maintained in contact with the subject body face away from the central portion 210.

The elongated portions 220 and 240 of the support structure 200 further comprise substantially rectangular slots 222 and 242, respectively, for receiving a strap or band for maintaining contact of portions or surfaces of the electrodes 122, 132, 142 and 152 (when the flexible electrode assembly 100 is mounted or accommodated in the support structure 200) with a contoured surface such as a portion of a human or animal body. When the strap or band is under tension, the resiliently deformable elongated portions 220, 230, 240 and 250 tend to flatten, thus providing improved contact between the electrodes and the contoured surface.

The support structure 200 may be made from plastic or another suitable material.

Figure 3:
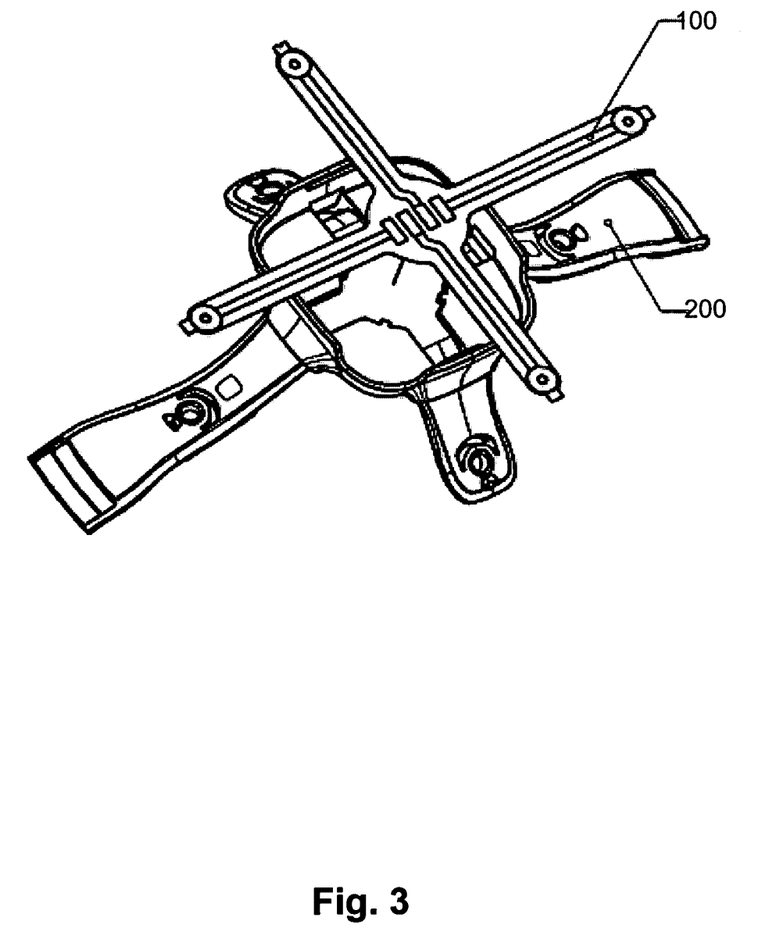
FIG. 3 is an exploded perspective view of assembly of the support structure of FIG. 2 with the flexible electrode assembly of FIG. 1.

FIG. 3 shows an exploded assembly view of the support structure 200 of FIG. 2 and the flexible electrode assembly 100 of FIG. 1. As described hereinbefore with reference to FIG. 2, the elongated portions 120, 130, 140 and 150 of the flexible electrode assembly 100 pass through the substantially rectangular slots 214, 215, 216 and 217 at the interface between the central portion and elongated portions of the support structure 200. The elongated portions 120, 130, 140 and 150 of the flexible electrode assembly 100 thus extend along the underside of a corresponding one of the elongated portions 220, 230, 240 and 250 of the support structure 200 and the portions or surfaces of the electrodes 122, 132, 142 and 152 that are to be maintained in contact with the subject body face away from the central portion of the support structure 200. The elongated portions 220, 230, 240 and 250 of the support structure 200 comprise slots on the underside thereof (not shown) into which the tabs 126, 136, 146 and 156 at the end of the elongated portions 120, 130, 140 and 150 of the flexible electrode assembly 100, respectively, are inserted upon assembly of the flexible electrode assembly 100 and the support structure 200. This arrangement ensures that the electrodes 122, 132, 142 and 152 are maintained in position. However, the skilled reader will appreciate that numerous other means for maintaining the electrodes and/or elongated portions of the flexible electrode assembly 100 may alternatively be practiced.

Figure 4:
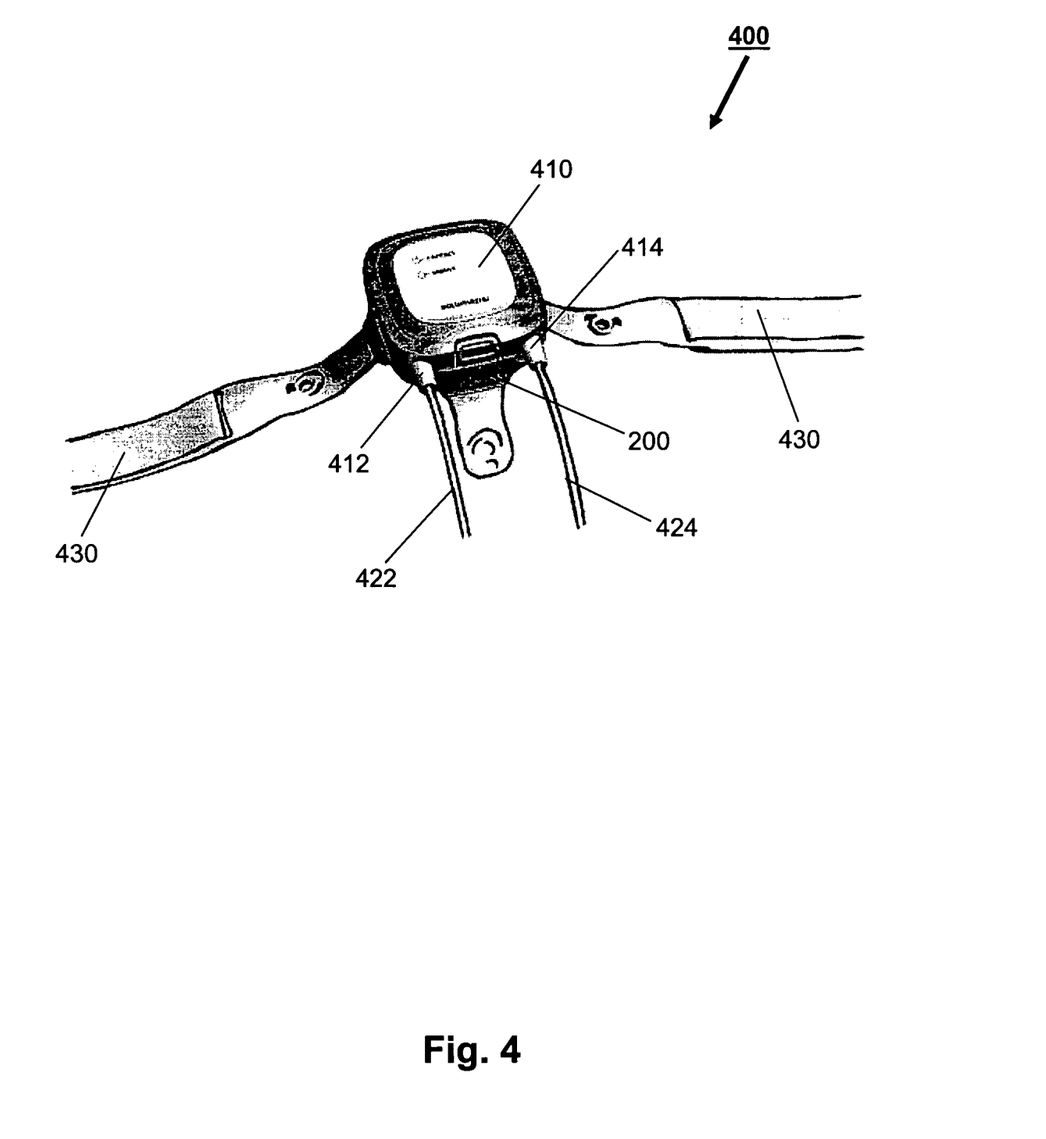
FIG. 4 is a perspective view of an apparatus for measuring electrophysiological signals in a human or animal body in accordance with an embodiment of the present invention.

FIG. 4 shows an apparatus 400 incorporating the support structure 200 of FIG. 2 and the flexible electrode assembly 100 of FIG. 1. An electronic circuit is mounted in a housing 410, which is in turn mounted on top of the support structure 200 of FIG. 2. The electronic circuit typically comprises an electronic amplifier that preferably exhibits high gain and low noise characteristics and is mounted on a printed circuit board. The printed circuit board comprises contact pins or surfaces, each of which are arranged to make electrical contact with a corresponding one of the electrical contacts 112, 114, 116 and 118 on the flexible electrode assembly 100 when the housing 410 is mounted on top of the support structure 200. The housing 410 and support structure 200 "snap-fit" together, the resulting compression ensuring that good electrical contact is maintained between the contact pins or surfaces on the amplifier printed circuit board and the corresponding electrical contact pins or surfaces on the flexible electrode assembly 100. This advantageously eliminates the need for solder connections between the electrodes and the input of the amplifier. The amplified output signals of the amplifier are delivered from the apparatus 400 via ports 412 and 414 and wires 422 and 424 (e.g., to a data recording apparatus). In an alternative embodiment, the apparatus 400 comprises a wireless transmitter and battery power source, which eliminates the need for the ports 412 and 414 and the wires 422 and 424.

The strap 430 is coupled to the ends of two of the elongate portions of the support structure 200 and may be elasticized to assist application of the apparatus 400 to a portion of a body (e.g., a head or torso).

Figure 5A:
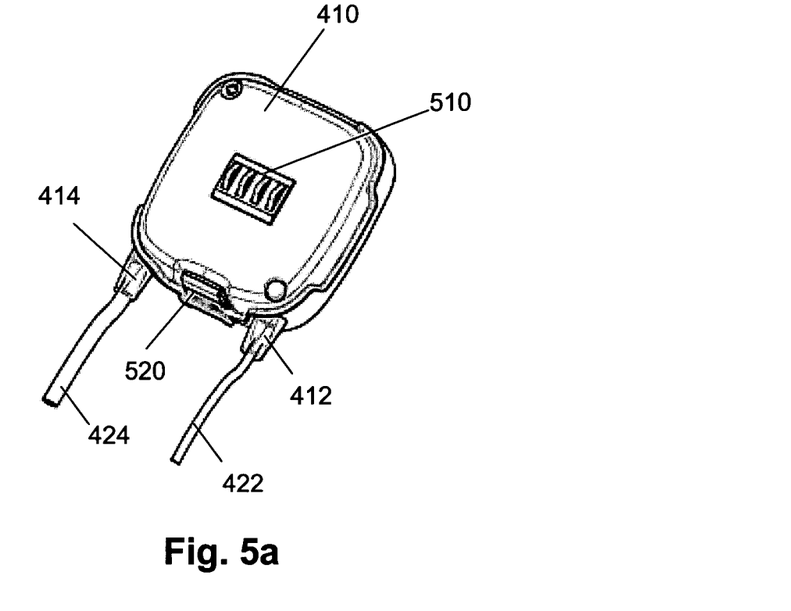
FIGS. 5a and 5b are a perspective bottom view and a perspective top view of a housing for an electronic circuit for mounting on the support structure of FIG. 2 as shown in FIG. 4.
Figure 5B:
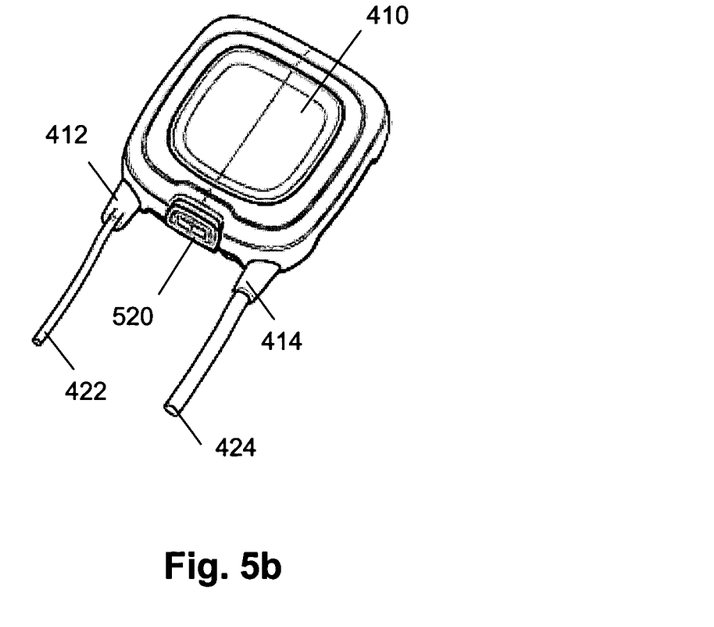

FIGS. 5a and 5b are a bottom perspective view and a top perspective view of a housing 410 for an electronic circuit that may be mounted on the central portion 210 of the support structure 200 of FIG. 2 in accordance with an embodiment of the present invention. FIG. 5a shows four spring-loaded electrical contacts 510, each of which are arranged to make electrical contact with a corresponding one of the electrical contacts 112, 114, 116 and 118 on the flexible electrode assembly 100 when the housing 410 is mounted on top of the support structure 200. The housing 410 and support structure 200 "snap-fit" together assisted by the retaining clip 520. The resulting compression ensures that good electrical contact is maintained between the spring-loaded electrical contacts 510 and the corresponding electrical contacts on the flexible electrode assembly 100. As discussed hereinbefore with reference to FIG. 4, this advantageously eliminates the need for solder connections in the electrically conductive path between the electrodes and an electronic circuit located in the housing 410. Output signals from the electronic circuit are delivered via ports 412 and 414 and wires 422 and 424, as described hereinbefore with reference to FIG. 4.

One application of the apparatus 400 is to measure visually evoked potentials (VEPs), which are useful for the diagnosis of glaucoma in humans. In this instance, the apparatus is applied to the occipital skull overlying the visual cortex of the brain (i.e., to the back of the head) and the strap 430 is disposed around the forehead to maintain contact between the electrodes of the apparatus 400 and the back of the head. However, embodiments of the present invention may be used to measure various different kinds of electrophysiological signals. For example, the apparatus 400 may be applied to the chest for ECG measurements. In this instance, the strap 430 would need to be of a length suitable for extending around the torso.

Flexible electrode assemblies in accordance with embodiments of the present invention include the actual electrodes as part of a flexible printed circuit board 101 (i.e., as a unitary structure). This advantageously avoids the need for separate conventional electrodes, each coupled by wires to an electronic signal processing apparatus, and the need for solder joints in the electrically conductive paths between the electrodes and the inputs of the amplifier and/or other signal processing circuit. Furthermore, flexible electrode assemblies in accordance with embodiments of the present invention are more economical to produce than conventional electrodes and may thus be disposable (e.g., on a patient-by-patient basis).

The foregoing detailed description provides exemplary embodiments only, and is not intended to limit the scope, applicability or configurations of the invention. Rather, the description of the exemplary embodiments provides those skilled in the art with enabling descriptions for implementing an embodiment of the invention. Various changes may be made in the function and arrangement of elements without departing from the spirit and scope of the invention as set forth in the claims hereinafter.

(Australia Only) In the context of this specification, the word "comprising" means "including principally but not necessarily solely" or "having" or "including", and not "consisting only of". Variations of the word "comprising", such as "comprise" and "comprises" have correspondingly varied meanings.

The invention claimed is:

1. An apparatus for measuring electrophysiological signals in a human or animal body, said apparatus comprising: a support structure comprising a central portion and a plurality of elongated portions extending radially outwards from said central portion, the central portion having a plurality of openings passing entirely through the support structure at respective interfaces between the central portion and the elongated portions; and a flexible electrode assembly comprising a central region having a plurality of electrical contacts, a plurality of elongated portions extending from the central region and each having a distal end spaced from the central region with an electrode disposed thereon, each electrode at the distal end coupled to one of the electrical contacts in the central region, said flexible electrode assembly mounted on said support structure such that said elongated portions of said flexible electrode assembly each extend through the openings and along a respective elongated portion of said support structure, wherein the electrode assembly is removably and repeatedly attached to the support structure; and a flexible printed circuit board disposed on at least one side of at least one elongated portion of the support structure and connecting said electrical contacts and said electrode, the flexible circuit board having a plurality of electrically-conductive through holes.

2. The apparatus of claim 1, wherein said plurality of elongated portions of said support structure are resiliently deformable.

3. The apparatus of claim 1, wherein said flexible electrode assembly is of unitary structure.

4. The apparatus of claim 1, wherein said flexible electrode assembly comprises a flexible electrode assembly in accordance with claim 1.

5. The apparatus of claim 1, further comprising an amplifier module for amplifying electrophysiological signals detected by said electrodes.

6. The apparatus of claim 5, wherein said electrodes are electrically connected to said amplifier by way of compressed contact of electrically conducting surfaces.

7. The apparatus of claim 2, further comprising attachment means for attaching said apparatus to a human or animal body.

8. The apparatus of claim 7, wherein said attachment means comprises a strap which, when under tension, causes said elongated portions of said support structure to deform such that contact between said electrodes and said human or animal body is substantially maintained.

9. The apparatus of claim 1, wherein said flexible electrode assembly is disposable.

10. An apparatus for measuring electrophysiological signals in a human or animal body, said apparatus comprising: an electrode assembly having a plurality of electrodes for detecting electrophysiological signals, the electrode assembly further including a central portion having a plurality of electrical contacts and a plurality of elongated portions extending radially outwards from the central portion, one or more of said elongated portions having one of the electrodes disposed thereon and coupled to one of the electrical contacts; a support structure for applying said electrodes to a human or animal body such that an electrically conductive path is maintained between said electrodes and said human or animal body, the support structure having a central portion and a plurality of elongated portions extending radially outwards from the central portion, wherein at least one of the central portion and the elongated portions of the support structure include a plurality of openings passing entirely through the support structure such that the elongated portions of the electrode assembly each extend through respective openings and along a respective elongated portion of the support structure; and a flexible printed circuit board disposed on at least one side of at least one elongated portion of the support structure and connecting said electrical contacts, the flexible circuit board having a plurality of electrically-conductive through holes and having an electronic circuit for processing said electrophysiological signals detected by said electrodes; wherein said electrodes and said electronic circuit are electrically connected by a solderless connection, and wherein the electrode assembly is removably and repeatedly attached to the support structure.

11. The apparatus of claim 10, wherein said electrodes and said electronic circuit are electrically connected by compressed contact of electrically conducting surfaces.

12. The apparatus of claim 10, wherein said electronic circuit is mounted in or to said support structure.

13. The apparatus of claim 10, wherein said electrodes form part of a flexible electrode assembly comprising:
   a central portion having electrical contacts disposed thereon; and
   a plurality of elongated portions extending radially outwards from said central portion, one or more of said elongated portions having an electrode disposed thereon;
   wherein said electrodes are electrically coupled to said electrical contacts disposed on said central portion.

14. The apparatus of claim 13, wherein said flexible electrode assembly comprises a flexible printed circuit board and said electrical contacts and said electrodes comprise conductive portions of said flexible printed circuit board.

15. The apparatus of claim 14, wherein said flexible electrode assembly comprises four of said elongated portions disposed at substantially 90 degree intervals around said central portion.

* * * * *